US00PP21844P2

(12) United States Plant Patent
Korlipara

(10) Patent No.: US PP21,844 P2
(45) Date of Patent: Apr. 5, 2011

(54) ***LEUCANTHEMUM* PLANT NAMED 'PALADIN'**

(50) Latin Name: *Leucanthemum×superbum*
Varietal Denomination: Paladin

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/653,603

(22) Filed: Dec. 14, 2009

(51) Int. Cl.
*A01H 5/00* (2006.01)

(52) U.S. Cl. ..... Plt./285

(58) Field of Classification Search ..... Plt./285
See application file for complete search history.

*Primary Examiner* — Kent L Bell
(74) *Attorney, Agent, or Firm* — Klarquist Sparkman, LLP

(57) ABSTRACT

A new and distinct *Leucanthemum* plant named 'Paladin' characterized by daisy type inflorescences with multiple layers of white ray florets and yellow orange disc florets, excellent bloom size, a medium, compact habit, well-branched flower stalks giving repeat bloom all summer, and excellent vigor.

1 Drawing Sheet

Botanical denomination: *Leucanthemum×superbum.*
Variety designation: 'Paladin'.

BACKGROUND OF THE INVENTION

The present invention relates to a new and distinct cultivar of *Leucanthemum* and given the cultivar name 'Paladin'. *Leucanthemum* is in the family Asteraceae. This new cultivar originated from an open pollinated cross between *Leucanthemum×superbum* 'Broadway Lights', an unpatented plant, as the seed parent, and an unknown pollen parent.

Compared to *Leucanthemum* 'Broadway Lights', the seed parent, the new variety is shorter and has white rather than light yellow new inflorescences and more ray florets.

Compared to *Leucanthemum* 'Anita Allan', an unpatented plant, the new variety has inflorescences that are larger, with thicker and more ray florets.

This new *Leucanthemum* cultivar is distinguished by:

1. daisy type inflorescences with multiple layers of white ray florets and yellow orange disc florets,
2. excellent bloom size,
3. a medium, compact habit,
4. well-branched flower stalks giving repeat bloom all summer,
5. and excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 2 year old plant growing in the ground in the garden in full sun in the field in late summer in Canby, Oreg.

FIG. 2 shows a close up of a inflorescence of *Leucanthemum* 'Paladin'.

DETAILED PLANT DESCRIPTION

The following is a detailed description of the new *Leucanthemum* cultivar based on observations of 1 year-old specimens growing in the ground in the field in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:
- *Type.*—Herbaceous perennial.
- *Hardiness.*—USDA Zones 4 to 9.
- *Size.*—50 cm wide and 56 cm tall to top of inflorescences.
- *Form.*—Basal clump.
- *Vigor.*—Excellent.

Stem (flowering):
- *Type.*—Ascending.
- *Size.*—Branching to 56 cm tall to a terminal inflorescence and 9 mm wide at base.
- *Internode length.*—2 cm to 4 cm.
- *Surface texture.*—Pubescent.
- *Color.*—Yellow Green 147B.

Leaf (basal):
- *Type.*—Simple.
- *Shape.*—Oblanceolate.
- *Arrangement.*—Basal.
- *Blade size.*—Grows to 12 cm long and 2.2 cm wide.
- *Margins.*—Coarsely serrate.
- *Apex.*—Acute.
- *Base.*—Attenuate, continuing down petiole.
- *Petiole.*—Grows to 6 cm long and 4 mm wide, pubescent, color closest to Yellow Green 146D.
- *Surface texture.*—Pubescent on both sides.
- *Venation.*—Pinnate.
- *Color.*—Top and bottom side, Green 137B.

Leaf (stem):

*Type.*—Simple, no petiole.

*Shape.*—Lanceolate.

*Arrangement.*—Alternate.

*Blade size.*—Grows to 12.5 cm long and 2 cm wide.

*Margins.*—Coarsely serrate on top ⅔, entire on bottom ⅓.

*Apex.*—Acute.

*Base.*—Clasping.

*Surface texture.*—Pubescent on both sides.

*Venation.*—Pinnate.

*Color.*—Topside, Green 139A, bottom side Green 137A.

Inflorescence:

*Type.*—Composite on terminal stalked heads.

*Number of flowering stems per plant in summer.*—About 50.

*Flowering stem.*—Grows to 56 cm tall from the base of the plant to the terminal Inflorescence to the base of a inflorescence head; branched, from 1 to 6 flowers per stem; leafy all the way up the stem; diameter growing to 8 mm wide near the inflorescence head; pubescent, younger stems Green 138A, older stems Green 138A heavily tinted Brown 200A.

*Size.*—Grows to 10 cm wide and 4.5 cm deep.

*Form.*—Ray petals cup downward slightly, mature disc is slightly rounded.

*Immature inflorescence.*—1.7 cm wide and 2.1 cm deep, outer ray florets held vertically and inner ray florets tilted inward and rolled up so only the back color shows, Yellow 2D, inside color Yellow White 158A.

*Ray florets.*—About 95 normal size in number (and 0 to 17 smaller size near the disc florets, grow to 32 mm long and 4 mm wide), lanceolate, obtuse, entire, attenuate, grows to 4.8 cm long and 1 cm wide, glabrous on both sides; top and bottom side White 155C with base Yellow Green 144B; pistil 1, Yellow Green 145D, 7 mm long, ovary 3 mm long, style 3 mm long, 2 branched stigma 1 mm long; no stamen.

*Disc.*—Slightly concave becoming convex, becoming 12 mm deep and 32 mm wide with maturity, Yellow Orange 14B.

*Disc florets.*—About 360 in number, each 5.5 mm long and 2 mm wide, corolla tubular campanulate, 3.5 mm long and 2 mm wide, 5 lobed, glabrous, Yellow Orange 14B; pistil 1, Yellow Green 145D, 5 mm long, ovary 3 mm long, style 3 mm long, 2 branched stigma 1 mm long; stamen 5 in number, 3 mm long and Yellow Orange 14B, pollen Yellow Orange 14B.

*Phyllaries.*—In 3 imbricate whorls, area 3.7 cm wide and 7 mm deep, lobes lanceolate in shape, grow to 12 mm long and 3 mm wide, Yellow Green 147B, margin membranous, tip obtuse, glabrous

*Receptacle.*—Grows to 10 mm wide and 4 mm deep, Yellow Green 145C.

*Bloom period.*—June through October in Canby, Oreg.

*Fragrance.*—Slight.

*Lastingness.*—Each inflorescence lasts about two weeks in Canby, Oreg.

Seeds: Average number of 3 seeds/head, each 3 mm long and 2 mm wide, oval, Brown 200C.

*Fertility.*—Poor.

Disease and pests: *Leucanthemum* are susceptible to aphids and leaf spots. These have not been observed on plants grown under commercial conditions in Canby, Oreg. No resistances are known.

I claim:

1. A new and distinct *Leucanthemum* plant as herein illustrated and described.

* * * * *

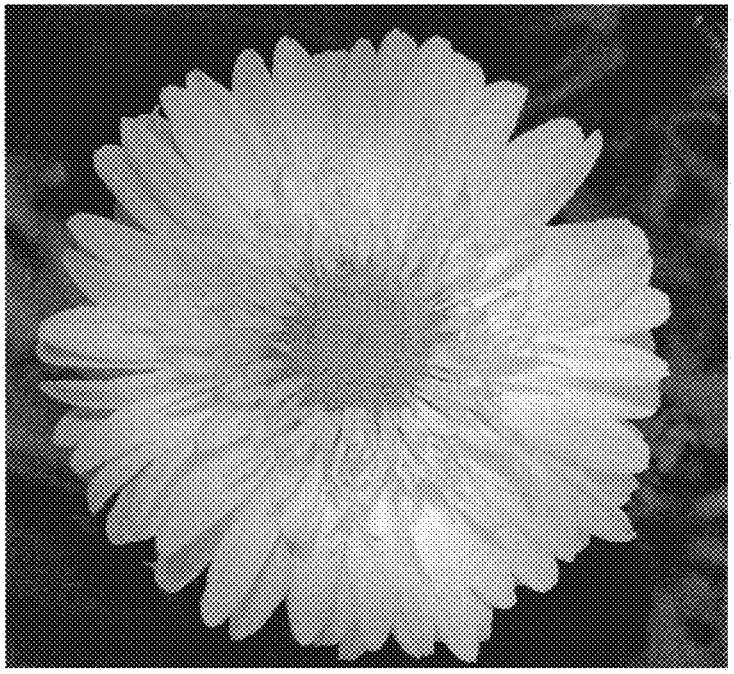

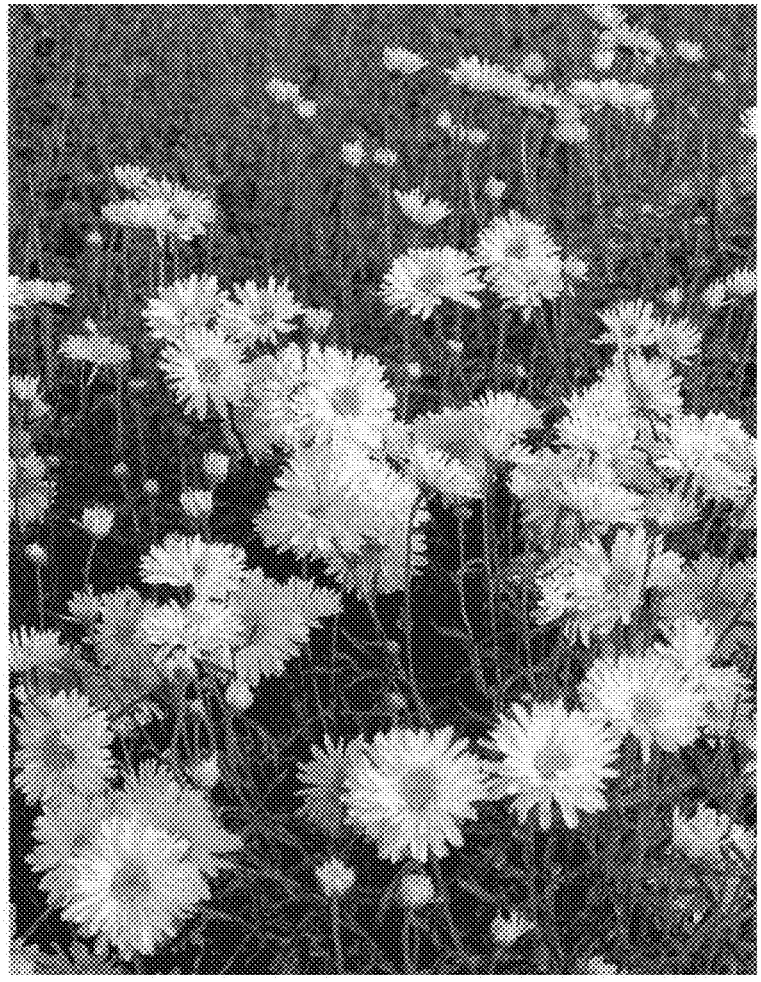
Figure 1 above,
Figure 2 below.